(12) United States Patent
Bezgachev et al.

(10) Patent No.: US 9,250,197 B2
(45) Date of Patent: Feb. 2, 2016

(54) LIGHTING DEVICE

(75) Inventors: Vitaly Bezgachev, München (DE);
 Marc Hemsendorf, München (DE);
 Christian Probst, München (DE);
 Stefan Recht, München (DE);
 Stephanus Wansleben, Berlin (DE)

(73) Assignee: GP Inspect GmbH, Planegg (DE)

( * ) Notice: Subject to any disclaimer, the term of this patent is extended or adjusted under 35 U.S.C. 154(b) by 1899 days.

(21) Appl. No.: 12/558,624

(22) Filed: Sep. 14, 2009

(65) Prior Publication Data

US 2010/0085749 A1 Apr. 8, 2010

(30) Foreign Application Priority Data

Sep. 12, 2008 (DE) .......................... 10 2008 047 085

(51) Int. Cl.
 *F21V 33/00* (2006.01)
 *G01N 21/95* (2006.01)
 *G01N 21/88* (2006.01)

(52) U.S. Cl.
 CPC ........ *G01N 21/9505* (2013.01); *G01N 21/8806* (2013.01)

(58) Field of Classification Search
 CPC .......... G01N 21/8806; G01N 21/9505; G01N 21/8803; G01N 21/88; G01N 21/8841; G01N 21/9501; G01N 21/9503; G01N 21/9506
 USPC ......... 362/186, 84, 235, 217.01, 217.05, 257, 362/296.01, 227, 231, 310, 138, 135, 140
 See application file for complete search history.

(56) References Cited

U.S. PATENT DOCUMENTS

| | | | | |
|---|---|---|---|---|
| 2,704,839 A | * | 3/1955 | Sweet | 362/542 |
| 3,061,715 A | * | 10/1962 | Thomas | 362/235 |
| 3,866,034 A | * | 2/1975 | Russo | 362/152 |
| 6,056,434 A | | 5/2000 | Champetier | |
| 7,327,450 B2 | | 2/2008 | Kreh et al. | |
| 2003/0012025 A1 | * | 1/2003 | Christen | 362/362 |
| 2004/0156195 A1 | * | 8/2004 | Robertson et al. | 362/186 |
| 2006/0227558 A1 | * | 10/2006 | Osawa et al. | 362/351 |
| 2007/0242451 A1 | * | 10/2007 | Richmond | 362/183 |
| 2009/0310350 A1 | * | 12/2009 | Dalton et al. | 362/235 |
| 2009/0313869 A1 | * | 12/2009 | Zemmouri et al. | 40/541 |
| 2010/0002425 A1 | * | 1/2010 | Tsai et al. | 362/223 |
| 2010/0033948 A1 | * | 2/2010 | Harbers et al. | 362/84 |

FOREIGN PATENT DOCUMENTS

| | | |
|---|---|---|
| DE | 202005010562 U1 | 10/2005 |
| DE | 69933494 T2 | 2/2007 |
| EP | 1494016 A2 | 1/2005 |

* cited by examiner

*Primary Examiner* — Thomas A Hollweg
*Assistant Examiner* — Kevin Quarterman
(74) *Attorney, Agent, or Firm* — Laurence A. Greenberg; Werner H. Stemer; Ralph E. Locher

(57) ABSTRACT

A method of examining an object containing a polycrystalline material, in which at least one part of the surface of the object is illuminated with substantially isotropic light, as well as a illumination device for carrying out the method. In this manner, the polycrystalline material is less influenced by the different reflection characteristics of individual particles of the polycrystalline material.

22 Claims, 7 Drawing Sheets

LIGHTING DEVICE

BACKGROUND OF THE INVENTION

Field of the Invention

The invention refers to a method for the examination of an object comprising polycrystalline material as well as an illumination device for carrying out the method according to the preamble of claim 7.

During the examination with light of objects comprising polycrystalline material, in particular objects consisting of polycrystalline material, different reflection characteristics and absorption characteristics of different particles of the polycrystalline material proved to be problematic. In principal, light means electromagnetic radiation of basically any frequency. In particular, it can be electromagnetic radiation with a frequency from a frequency range extending from the near near-ultraviolet range up to far infrared range. The light can be composed of electromagnetic radiation of different frequencies or can be monochromatic.

The different reflection characteristic of different particles is based mainly on the different orientation of the different particles. Hence, when looking for example at a polycrystalline material with the naked eye under normal ambient conditions individual particles appear brighter while others appear darker depending on the perspective. This has the effect that during the examination and inspection of objects which comprise a polycrystalline material the signal obtained from the particle structure superimposes the signals to be detected, respectively. This complicates for example the automatic or semi-automatic detection of ruptures or other material defects in such objects. This also includes impurities, depositions, or the like whose detection is also complicated due to different reflection characteristics of individual particles of the particle structure.

In addition, provided that they are arranged on a polycrystalline material, the examination of non-polycrystalline materials can be complicated due to the different reflection characteristics. For example, the optical determination of the thickness of per se homogeneous and non-polycrystalline layers can be inhibited if they are arranged for example on a polycrystalline substrate because reflections at the polycrystalline material and thus the different reflection characteristics of different particles influence the optical determination.

BRIEF SUMMARY OF THE INVENTION

Against this background, it is the object of the present invention to provide a method for the examination of an object comprising a polycrystalline material which is less influenced by the different reflection characteristics of individual particles of the polycrystalline material.

The object is solved by a method comprising the features of claim 1.

It is a further object of the present invention to provide an illumination device for carrying out the method.

This object is solved by an illumination device with the features of claim 7.

Beneficial further embodiments are subject of respective dependent claims.

The method of the present invention provides for illuminating a surface of the object to be examined with substantially isotropic light. It has been shown that in this manner the particle structure of the polycrystalline materials can be largely circumvented, i.e. different reflection and absorption characteristics of different particles do not emerge or at least emerge only to a much lesser extent. The examination and inspection of the object is less influenced by the particle structure, respectively.

In a further embodiment of the present invention, the surface of the object to be examined is illuminated not only with substantially isotropic but at the same time substantially homogeneous light which has the effect that the surfaces appear in a grayscale illustration known in the art of image processing as regularly grey, under ideally complete circumvention of the particle structure—disregarding other complications, such as material defects. Other properties of the object can be more easily identified in front of this regular background since no intensity fluctuations appear due to inhomogeneity in the illumination.

To what extent the particle structure as described can be circumvented due to the use of substantially isotropic light depends on the extent in which isotropic light is used. With progressive decrease of isotropy, the particle structure can be less circumvented until at last the particle structure clearly emerges under complete anisotropic illumination. For example, some particles show a complete absorption while others show a total reflection.

The advantage produced by the use of homogeneous light depends in a similar manner from the degree of homogeneity. Using complete homogeneous illumination, a disturbance of the examination through locally different illumination intensities can be completely eliminated whereas increasing inhomogeneous illumination can decrease a disturbance much lesser.

It has been shown that the method of the present invention can be used in a preferred manner for the examination of solar cell substrates. In particular when using polycrystalline silicium solar cell substrates, the particle structure can be effectively circumvented so that the solar cell substrate can be examined without or at best with only little disturbance through the particle structure.

As it has been found, material defects can be detected in a preferred manner with the method of the present invention because the material defects can be better identified due to the at least partially masked particle structure. A material defect means for example, ruptures, in particular conchate disruptions, chippings but also impurities or depositions.

Furthermore, the method of the present invention can be used in a preferred manner to examine materials or material systems which are associated with a polycrystalline material, in particular when the materials or the material system is applied on it. For example, dielectric layers can be examined which were applied to a polycrystalline material. In particular the thickness of the applied layers can be determined more reliably because disturbing influences of the particle structure can be eliminated at least substantially with the method of the present invention. In a particular preferred embodiment antireflection coatings are examined, in particular their thickness is determined, wherein the antireflection coatings are arranged on an object which comprises polycrystalline material. For example, the antireflection coatings are arranged on a polycrystalline silicium substrate. It is apparently not only possible to examine single coatings but also whole coating systems, for example antireflection coating systems with several layers made of different materials, such as titanium oxide and magnesium difluoride. Single layer systems of silicium nitrite or silicium dioxide can apparently also be examined in a preferred manner.

In a preferred embodiment an antireflection coating or antireflection coating system is examined by detecting and analyzing light of different wavelengths which is reflected by the surface of the object to be examined. In this manner, the reflection characteristics of the object to be examined can be determined at different wavelengths which can be of particular advantage for determining the thickness of single layers of coating systems. Therefore, the object to be examined is preferably illuminated in chronological steps with light of different wavelengths and the intensity of the reflected light is determined with a detector, for example with a monochromatic camera. In this way an easy to handle monochromatic detector can be used. A simultaneous illumination with light of different frequencies is apparently also possible in connection with the use of a detector with corresponding spectral resolution.

It has been shown that the method of the present invention can be used not only for coatings but can also be used in a preferred manner in connection with other surface treatments. For example, surface texturing, such as a surface texturing which is used for solar cell substrates to increase the light coupling into the solar cell substrate, can be examined comfortably. In particular the quality and homogeneity of the surface texturing, which is often applied using wet-chemical etching, can be inspected.

As described above, the method of the present invention allows masking the particle structure, wherein the circumvention is so much more efficient the higher the isotropy of the light that is used for illumination. Depending on which property of an object is to be examined a stronger or weaker circumvention of the particle structure might be necessary. Thus, the degree of isotropy needs to be adapted depending on the individual application.

The illumination device of the present invention for carrying out the method comprises a hollow body which is coated on its inner surface with a light reflecting layer. The hollow body itself comprises two spherical caps which are connected to each other via a tube. A surface to be illuminated can be illuminated using substantially isotropic light with such an illumination device. The isotropic light is thereby generated in that beams of light originating from one or more light sources are repeatedly reflected at the reflective layer before their incidence at the surface to be illuminated. The fraction of the isotropic light is the larger the more spherical and larger the hollow body is. Hence, in the ideal case the hollow body is an integrating sphere with a diameter as large as possible.

As described above, in practice a sufficient circumvention of the particle structure can already be realized when using light which is not completely isotropic. This finding is used by the illumination device of the present invention in that instead of providing a hollow body a hollow body with a maximized diameter is provided which comprises two spherical caps which are connected to each other via a tube. It has been shown that in this way the surface to be illuminated can be illuminated with enough isotropic light.

Thus, the geometrical shapes of the spherical cap and tube are to be interpreted broadly. Although deviations from the ideal spherical cap form or tubular form, for example due to openings, mouldings or shapes, result in a further decrease of the light's isotropy, the remaining fraction of isotropic light can be sufficient for the respective application to sufficiently circumvent the particle structure. Thus, the term tube is to be understood broadly. In this connection, a tube can be understood on the one hand as an ideal hollow cylinder and on the other hand can be understood for example as a hollow cone whose circumferential surface comprises non ideal forms, such as dents or other mouldings or shapes. In general, an elongated hollow body can be used which comprises any kind of geometry which is stretched in the direction of its opening. To what extent such an irregularly formed tube can provide enough isotropic light can be examined based on the requirements of the respective application. The term spherical cap is to be understood in a similar broad manner. For example a spherical cap can comprise an opening at its pole so that in a strict geometrical sense it cannot be spoken any longer of a spherical cap but rather a spherical zone. In case of the present invention however, this spherical zone constitutes a spherical cap, namely one with an opening at the pole of the spherical cap.

In contrast to an integrating sphere with a maximized diameter, the illumination device of the present invention can be designed in an area saving manner. In providing the tube between the two spherical caps, incident light can be reflected more often before it incidents on a surface to be illuminated which is not the case when using an integrated sphere comprising a diameter which is corresponding to the smallest possible volume expansion of the illumination device of the present invention. Such an integrated sphere would not comprise in any spatial direction a larger expansion than the smallest spatial volume expansion of the illumination device of the present invention. As a result of the described increased number of reflections, the illumination device of the present invention can provide light with a higher degree of isotropy than an integrating sphere which uses a similar area.

Despite the description of possibilities to save area, the illumination device of the present invention allows to provide sufficient space for a comfortable operation and comfortable conduction of maintenance operations as well as space for installing further equipment at the inside of the hollow body, respectively. This is a result of stretching the hollow body in the longitudinal direction of the tube, which is effectuated by the tube which is inserted between the spherical caps. The extension of the tube in its longitudinal direction can in practice be selected to be as large so that in the respective application the necessary acts for maintaining and operating can be carried out comfortably and so that enough space is provided for necessary equipment, in particular measuring equipment.

In other words, the illumination device of the present invention allows providing sufficient amount of isotropic light and at the same time allows saving area in one plane, wherein the plane extends substantially perpendicular to the longest direction of expansion of the illumination device. Thus, the illumination device of the present invention can save area in one plane provided that enough space is provided in a direction which is almost perpendicular to this plane. Therefore, the illumination device of the present invention is capable of being integrated in production lines in an area saving manner.

As has already been described above, the spherical cap or tube can deviate more or less from the ideal spherical cap shape and tubular shape depending on the respective application, respectively. Nevertheless, a particle structure is circumvented more efficiently the larger the fraction of isotropic light. Considering this background, in a preferred embodiment of the present invention spherical caps are based on spheres having the same radius. In addition, the spherical caps have the same height which further increases the fraction of isotropic light. Moreover, spherical caps having the same radii and same heights can be easily connected to each other using a hollow cylinder.

In one preferred embodiment of the illumination device of the present invention, for the purpose of further increasing the fraction of isotropic light, the spherical caps are designed as hemispheric shells. In particular, hemispheric shells of spheres with the same radius are preferred so that the spherical caps which are designed in the form of two hemispheric shells form a sphere together. This again allows to easily connect the hemispheric shells together via a hollow cylinder, wherein the radius of the hollow cylinder is corresponding to the radius of the hemispheric shells.

Construction of the tube in form of a hollow cone allows an easy and thus preferred connection of spherical caps when using hemispheric shells having different radii or when using corresponding ulterior designs of the two spherical caps.

In a preferred embodiment of the device of the present invention a closable service opening is provided in the hollow body to allow an easy access for maintenance works or operations works. To simplify matters, this service opening is arranged in the area in which the tube is arranged. The capability to be closed can be obtained by providing a door.

In a preferred embodiment, the reflective coating is at least partially realized as Lambertian emitter, i.e. the reflective layer acts at least for one wavelength of the utilized electromagnetic radiation as Lambertian emitter. A Lambertian emitter refers to a material which reflects incident light in such a way that the radiant emittance of the reflected light is independent from the viewing angle. By means of such a reflective layer largely isotropic and homogeneous light can be generated due to multiple reflections at the layer. When using light in a spectral region which is visible for humans or partially also when using light of other wavelengths barium sulfate can be used for example as reflective layer.

In a preferred embodiment of the illumination device of the present invention, illuminants are provided which are arranged in a way so that the surface to be illuminated can be illuminated only indirectly. Thus, fractions of anisotropic light can be further reduced. Preferably, different kinds of illuminants can be used which at least partially emit light of different frequencies. For example, a first kind of illuminant emits red light while a second kind of illuminant emanates blue light. By operating only one kind of illuminant at the same time, it is possible to carry out examinations in chronological order with light of different frequency. For example, this way the reflection characteristic of a surface to be illuminated can be examined using light at different frequencies. In general all kinds of known illuminants can be used, in particular light-emitting diodes, which are simply called LEDs. On the one hand LEDs are obtainable for multiple light frequencies and on the other hand they can emit collimated light without the need of using complicated ancillary optics, which facilitates to guarantee an indirect illumination.

One embodiment of the present invention provides a further illuminant which is at least partially suitable to directly illuminate the object to be illuminated. Thus, whenever required, anisotropic light can be selectively used. This at least one further illuminant is arranged preferably in the tube, more preferably in a drilled hole which is comprised in the tube. However, in general it can be comprised in any position of the hollow body as long as this configuration allows a direct illumination of the surface to be illuminated.

In a preferred embodiment of the illumination device of the present invention, the surface to be illuminated is capable of being arranged in a spherical cap. The surface to be illuminated is preferably capable of being arranged so that it is facing the tube. In one embodiment, one of the spherical caps comprises an auxiliary opening through which a surface to be illuminated can be placed inside the hollow body. Thus, the surface to be illuminated can be positioned in the illumination device without any problems. Furthermore, it is possible to automatically or semi-automatically load the illumination device with the surface to be examined, which is preferred with respect to integration of the illumination device of the present invention in an automated or semi-automated production line.

In an alternative embodiment of the illumination device of the present invention, one of the spherical caps comprises an auxiliary opening through which a surface of an object to be illuminated which is positioned outside the hollow body can be illuminated. Thus, the surface to be examined can stay outside the hollow body during the examination. Compared to a position at the inside of the hollow body this might result in a decrease of the fraction of isotropic light, but it has been shown that the percentage of isotropy of the light can be enough for a sufficient circumvention of the particle structure, whereby this depends on the specific application. If the percentage of isotropy is sufficient the alternative embodiment just described facilitates the integration of the illumination device in an automated or semi-automated production line. In addition, time for loading of the surface in the hollow body can be spared.

In all alternative embodiments, the auxiliary opening is preferably positioned in the area of the cap of the respective spherical cap.

In a preferred embodiment of the present invention, illuminants are arranged in one of the spherical cups. Preferably, they are arranged in drilled holes which are comprised in the spherical cap. Henceforth, servicing of the illuminants or their operation can be carried out comfortably from the outside of the hollow body. Irrespective of the question whether they are arranged in drilled holes or not, particularly preferred are illuminants which are arranged in the spherical cap which comprises an auxiliary opening or in which the surface to be illuminated can be positioned. In case the surface to be illuminated is positioned in the spherical cap, the illuminants are preferably arranged so that a direct illumination, which originates from the illuminants towards the surface to be illuminated, is excluded. This way, the threat of a direct illumination of the surface to be illuminated and thus an increased anisotropic fraction of light can be reduced. To achieve a preferably homogeneous light the illuminants are preferably arranged in a circular arrangement.

In a preferred embodiment of the present invention, a detector opening is comprised in one of the spherical caps. Thus, a detector used herein can be arranged partly outside the hollow body so that the reflection of light inside the hollow body is less affected. This can be of particular advantage when using voluminous detectors. A camera, in particular a monochromatic camera can be preferably used as detector. The detector opening is preferably comprised in the spherical cap which houses neither the auxiliary opening nor the surface to be illuminated.

In the following the present invention is described in more detail with reference to the Figures. If it is practicable, the same reference signs are used for elements having the same technical effect. It is shown:

DESCRIPTION OF THE INVENTION

Figure 1:
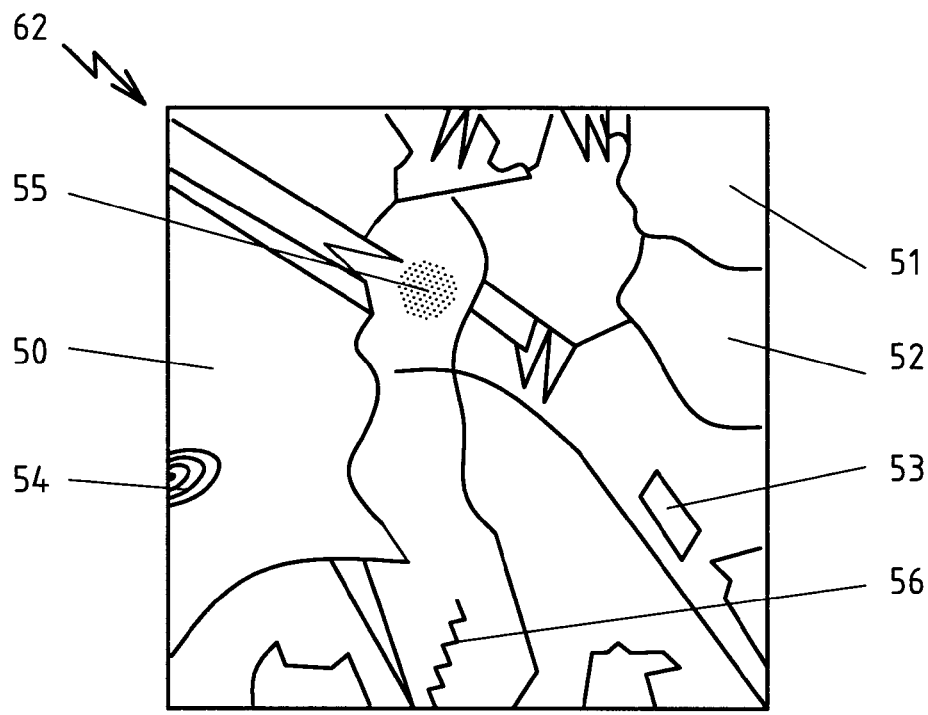
FIG. 1 Top view of a polycrystalline silicium wafer according to the prior art in a schematic illustration.

FIG. 1 shows as an example for a polycrystalline material 50 a polycrystalline silicium wafer 62 according to the prior art. Single particles, for example particles 51, 52, 53 of the polycrystalline material 50 can be clearly identified. Furthermore, schematic material defects are illustrated, which are to be detected during an examination of the silicium wafer 62, in particular during an examination by means of an optical detection. Schematically shown are for example a conchate disruption 54, a rupture 56, as well as an impurity 55, such as a finger print. Detection of the defects 54, 55, 56 turns out to be problematic due to the different reflection characteristics and absorption characteristics of the different particles 51, 52, 53. Therefore, a need exists to largely circumvent the normally well recognizable particle structure which appears under ambient conditions, and results from the different reflection characteristics and absorption characteristics, respectively.

Figure 2:
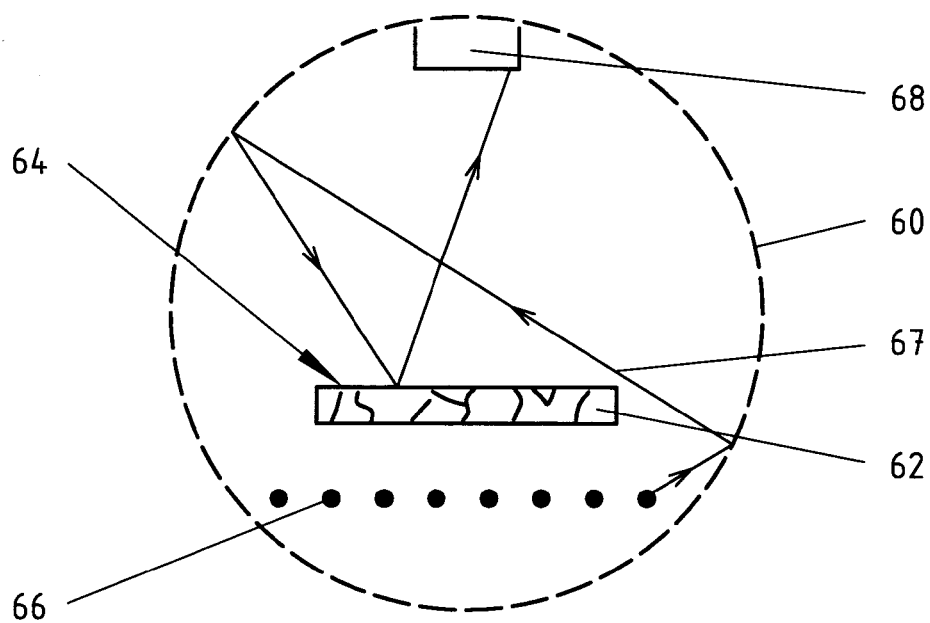
FIG. 2 Schematic illustration of the method of the present invention using an integrating sphere.

FIG. 2 illustrates a schematic illustration of the method of the present invention which allows the aforementioned. As an example for an object comprising a polycrystalline material a silicium wafer 62 is shown, whose surface 64 is to be examined. For this purpose the surface 64 of the silicium wafer 62 is illuminated with substantially isotropic light 67. The isotropy of the light is effected by light beams emitted by illuminants 66, wherein the light beams are reflected multiple times by an almost ideally reflecting inner surface of the integrating sphere 60, which is illustrated schematically with dashed lines, before the light beams incident at the surface 64 of the silicium wafer 62 to be illuminated, as it is schematically shown for one light beam of which the ray path is shown. The substantially isotropic light results from the synopsis of the plurality of emitted light beams which are all reflected several times so that at the end substantially isotropic light incident the surface 64 of the silicium wafer 62. Reflected by the surface the light reaches the detector 68 which detects 68 the reflected light and thus allows examination of the object. Further processing of the detector signals is possible depending of the specific application.

As previously mentioned further above, the method is preferably used for the detection of material defects. However, besides this application, many other further application possibilities exist, such as the possibility to examine the surface texturing, preferably the quality and homogeneity of the surface texturing. Surface textures are used for example for the manufacture of solar cells for increasing the light coupling into the solar cell substrate.

Figure 3:
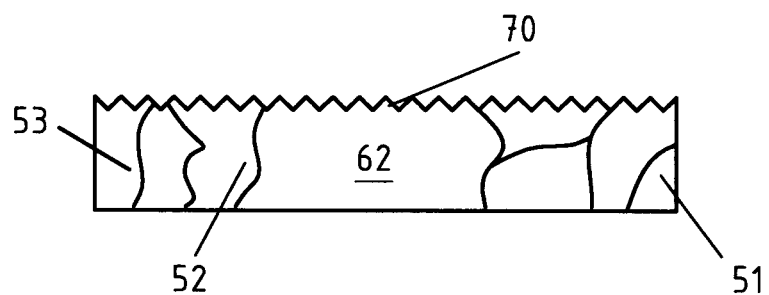
FIG. 3 Cross sectional view of a polycrystalline solar cell substrate having a surface texture according to the prior art in a schematic illustration.

FIG. 3 shows again a schematic illustration of a silicium wafer 62 made of polycrystalline material wherein again the single particles 51, 52, 53 can be identified. This silicium wafer comprises at one side a surface texture 70. When examining this surface texture 70 it was shown that by using the method of the present invention the interfering particle structure can preferably be circumvented. Examination in the context of the present application refers in the end to any kind of examination method in which electromagnetic radiation reflected by the object to be examined is used.

The method of the present invention further proved useful for the examination of layers or layer systems, which are deposited on a polycrystalline material.

Figure 4:
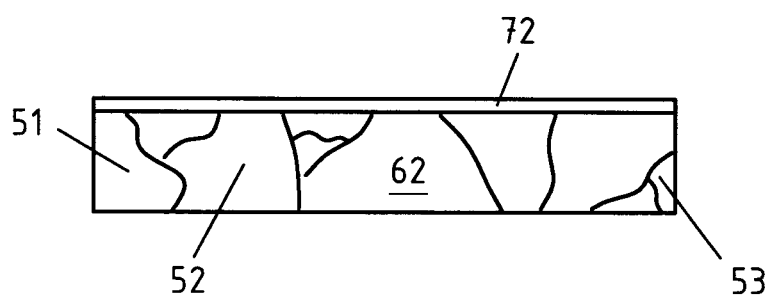
FIG. 4 Schematic cross sectional view of a polycrystalline solar cell substrate having an antireflection coating according to the prior art.

FIG. 4 shows exemplarily a polycrystalline silicium wafer 62 which is furnished with an antireflection coating 72. For the examination of this antireflection coating or also other layers or layer systems, the particle structure originating from the different reflection characteristics and absorption characteristics of the different particles 51, 52, 53 can be sufficiently circumvented.

Figure 5:
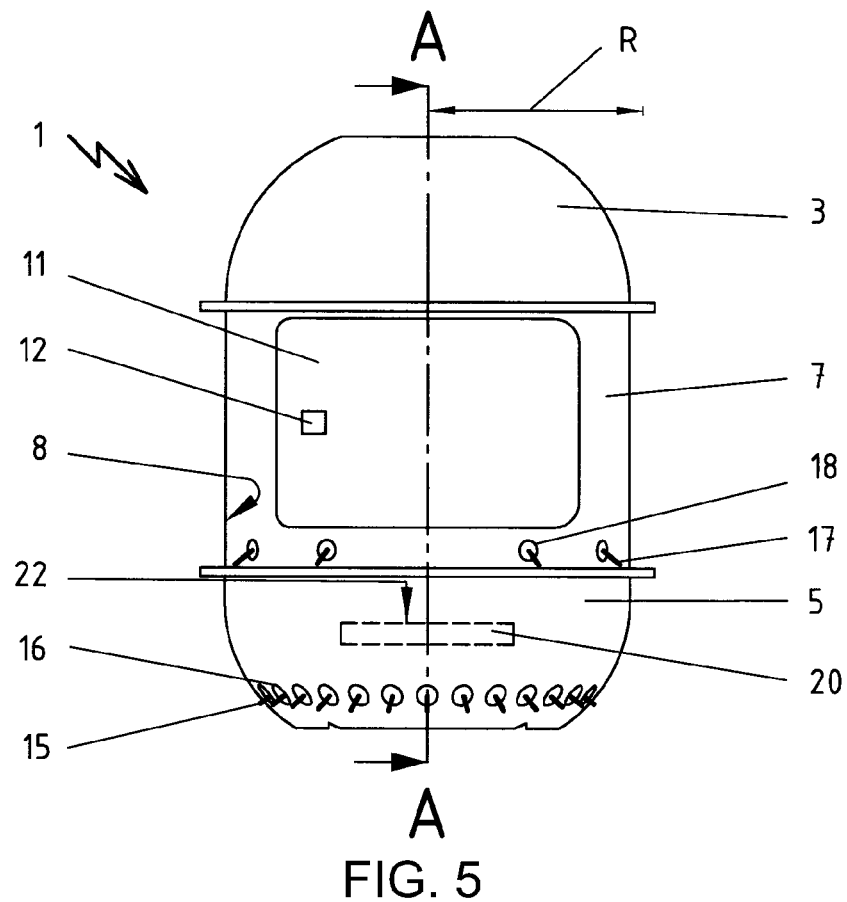
FIG. 5 Front view of a first embodiment of an illumination device of the present invention.

FIG. 5 shows schematically a front view of a first embodiment of an illumination device of the present invention 1. It comprises a hollow body which is assembled of two hemispheric shells 3, 5 and a hollow cylinder 7. At the inner surface 8 the hollow body, as can be seen in the cross sectional view of FIG. 7, comprises a reflective layer 13 which is preferably selected to provide a Lambertian emitter.

In the area of the hollow cylinder 7 the illumination device 1 comprises a service opening 9 which is shown in the illustration in FIG. 5 to be closed by a door 11, wherein the door 11 can be operated with a door handle 12.

In the embodiment of FIG. 5 the solar cell substrate 20 is positioned inside the hollow body 3, 5, 7 as an example for an object to be examined which is shown in the illustration of FIG. 5 with dashed lines. The surface of the solar cell substrate 20 serves in this embodiment as the surface 22 to be illuminated which in the present case faces the hollow cylinder. For the generation of light in the embodiment shown in FIG. 5 LEDs 15 are provided for indirect illumination of the surface to be illuminated 22. These LEDs 15 are arranged in a circular shaped arrangement at the lower end of the hemispheric shell, in which also the solar cell substrate 20 is arranged. As shown in FIG. 5, the LEDs 15 are positioned below the surface 22 of the solar cell substrate 20 which is to be illuminated. This way it can be largely avoided that light emitted by the LEDs 15 reaches the surface to be illuminated 22 directly.

As shown in FIG. 5, the LEDs 15 are preferably arranged so that they emit light from the bottom to the top into the hollow body such that the light is reflected at the reflective layer 13 as often as possible before it incidents the surface of the object to be illuminated 22 and the solar cell substrate 20, which are capable of being arranged in the spherical cap 5, respectively. This way, substantially isotropic light can be provided. Isotropy of the light can be improved by positioning the object to be illuminated, in the present case the solar cell substrate 20, as close as possible to the side of the cap of the hemispheric shell 5 that means in the illustration in FIG. 5 preferably at the bottom. If for the respective hemispheric shell 5 an auxiliary opening 24 for introducing the surface to be illuminated 22 into the hollow body 3, 5, 7 is provided, as it is the case in the illustrated embodiment, the surface to be illuminated 22 is to be positioned as close as possible to this auxiliary opening 24 to increase isotropy of the light. It should be considered that a direct illumination via LEDs 15 is still to be avoided. Otherwise the gain of isotropy can be compensated or even overcompensated through direct illumination effects in an arrangement in which the surface to be illuminated 22 is arranged very close to the auxiliary opening 24 and the cap of a closed hemispheric shell 5, respectively.

In the embodiment shown in FIGS. 5 to 10 the LEDs 15 are arranged in a circle at the lower hemispheric shell 5 so that as much as possible of a homogeneous light is generated. In addition they are positioned in drilled holes 16 which on the one hand allows comfortable accessibility for servicing works from the outside of the hollow body and on the other hand results in a marginal impairment of the surface structure of the inner surface 8 of the hollow body.

For the LEDs 15 for indirect illumination of the solar cell substrates different kind of LEDs can be used, which emit light of different frequencies. This way, examinations, as described above, can be carried out at the same time or in chronological order at different wavelengths.

The already mentioned auxiliary opening 24 for introducing the surface to be illuminated 22 allows a free view of the object to be examined which can be advantageous in certain kind of applications. In addition, the illumination device can be loaded automatically or semi-automatically which allows integration of the illumination device in an automated or semi-automated production line, which is partially called an inline-production line. On the other hand, the auxiliary opening 24 leads to a loss of isotropy so that for specific applications it needs to be examined whether it is advisable to provide an auxiliary opening 24 or not. It has however been shown that if otherwise the configuration of the hollow bodies 3, 5, 7 benefits isotropy, the use of an auxiliary opening 24 allows in general to sufficiently circumvent the particle structure.

In the embodiment shown in FIGS. 5 to 10, in addition to the LEDs 15 further LEDs 17 can be comprised for a partial direct illumination of the surface to be illuminated 22 of the solar cell substrate 20 and an object in general, respectively. This way, one can also comfortably carry out an examination using anisotropic light, which can be beneficial for specific examinations. To ensure that the surface of the inner side 8 of the hollow body 3, 5, 7 is less affected, the LEDs 17 are again arranged in bores 18.

Figure 6:
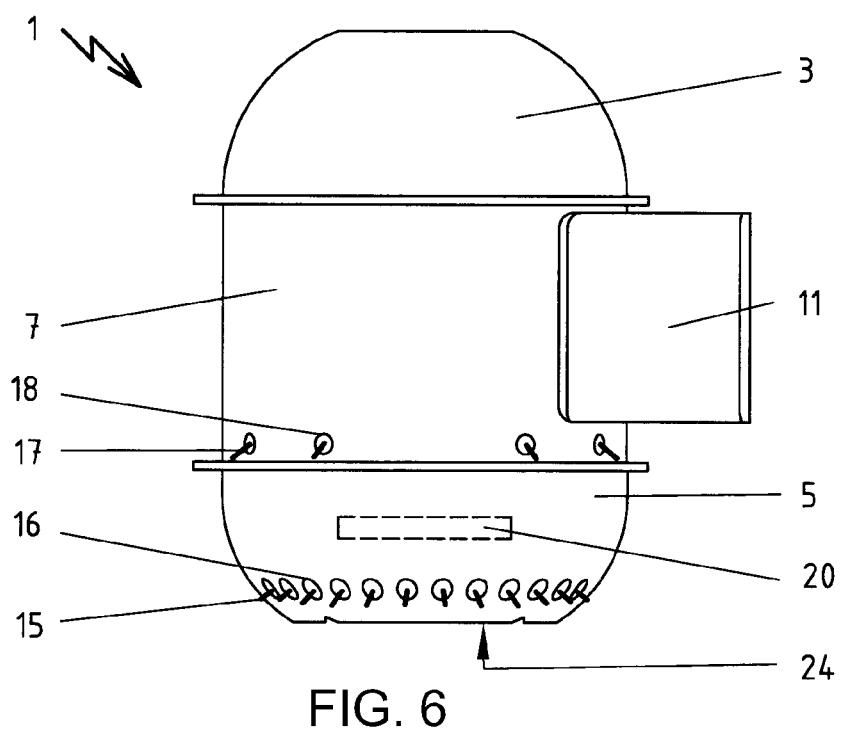
FIG. 6 Side view of the embodiment shown in FIG. 5.

The illustration in FIG. 6 shows the illumination device of FIG. 5 in a side view, wherein the solar cell substrate 20, which cannot be seen in this perspective, is again indicated with dashed lines to indicate its position. In contrast to the illustration in FIG. 5, the door 11 is open in the illustration in FIG. 6.

Figure 7:
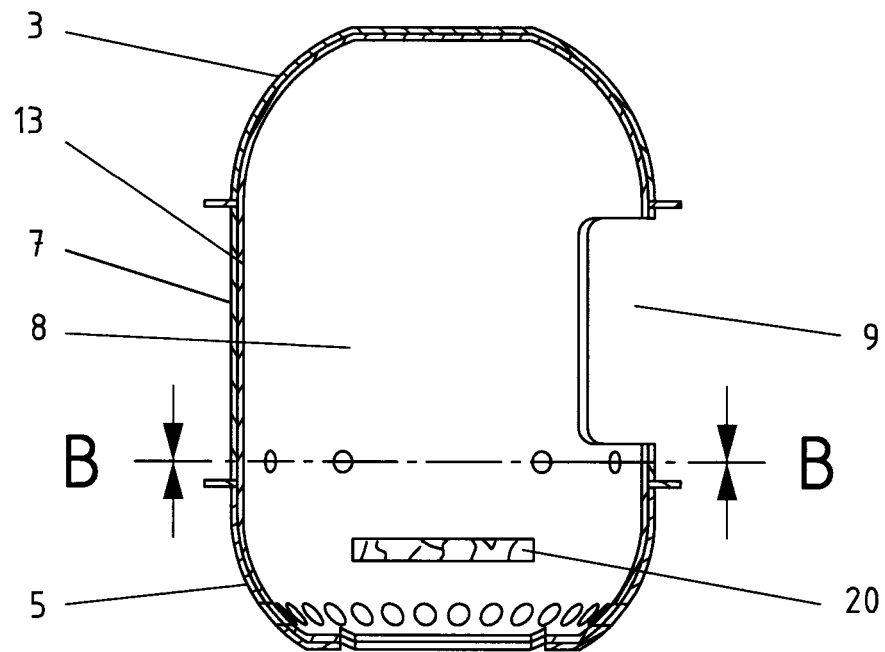
FIG. 7 Cross sectional view along A-A of the embodiment shown in FIG. 5.

FIG. 7 shows a cross sectional view through the illumination device shown in FIG. 5 along the line A-A. In this Figure the already mentioned reflective layer 13 can be clearly seen. Furthermore, the polycrystallinity of the solar cell substrate 20 becomes apparent. In the illustration of FIG. 7 the door 11 is not shown so as to be better able to recognize the auxiliary opening 9.

Figure 8:
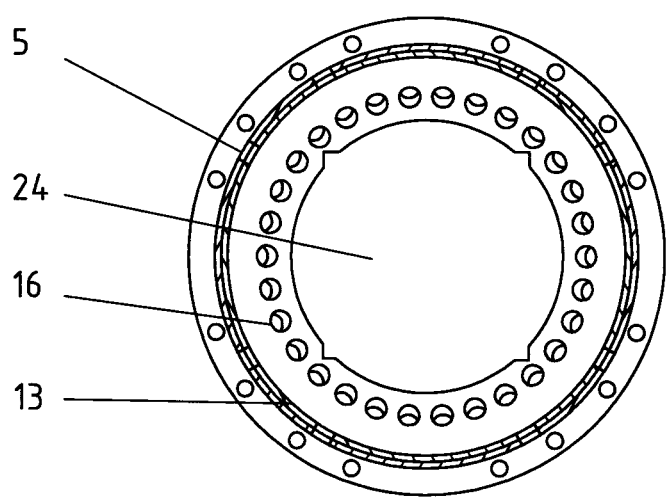
FIG. 8 Cross sectional view downwards along B-B of the embodiment shown in FIGS. 5 to 7.
Figure 9:
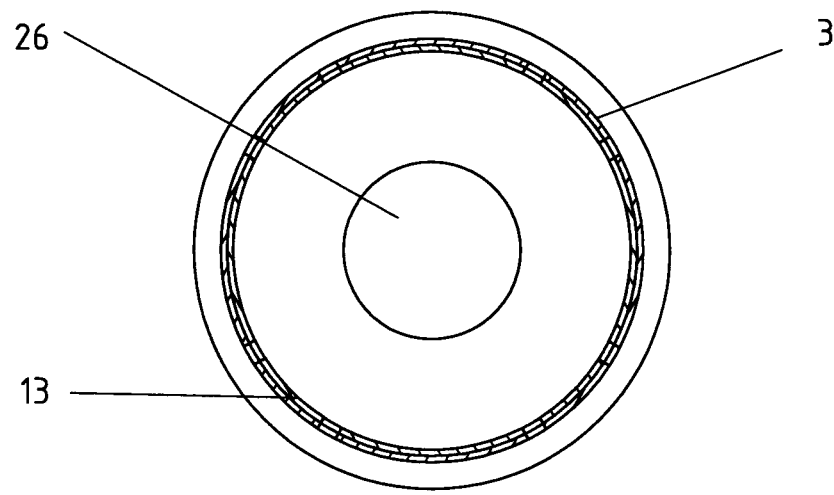
FIG. 9 Cross sectional view upwards along B-B of the embodiment shown in FIGS. 5 to 7.

FIG. 8 shows a cross sectional view of the illumination device shown in FIGS. 5 to 10 along the line B-B shown in FIG. 7. Thereby, the line of sight in the downwards direction of the hemispheric shell 5 is illustrated. In this illustration the auxiliary opening 24 is clearly recognizable in addition to the reflective layer 13.

The illustration shown in FIG. 9 shows again a cross sectional view of the illumination body shown in FIGS. 5 to 10 along the plane indicated by line B-B in FIG. 7, however, this time with the line of sight upwards, which is facing towards the hemispheric shell 3. In this line of sight, the reflective layer to be provided at the inner surface 8 of the hollow body and also a detector opening 26 can be seen. Above or partially in this opening a detector 30 is comprised as it is schematically indicated in the exemplary illustration of projection of FIG. 10. In the embodiment shown the detector is a camera 30 but in general any kind of known and suitable detector can be used.

Figure 10:
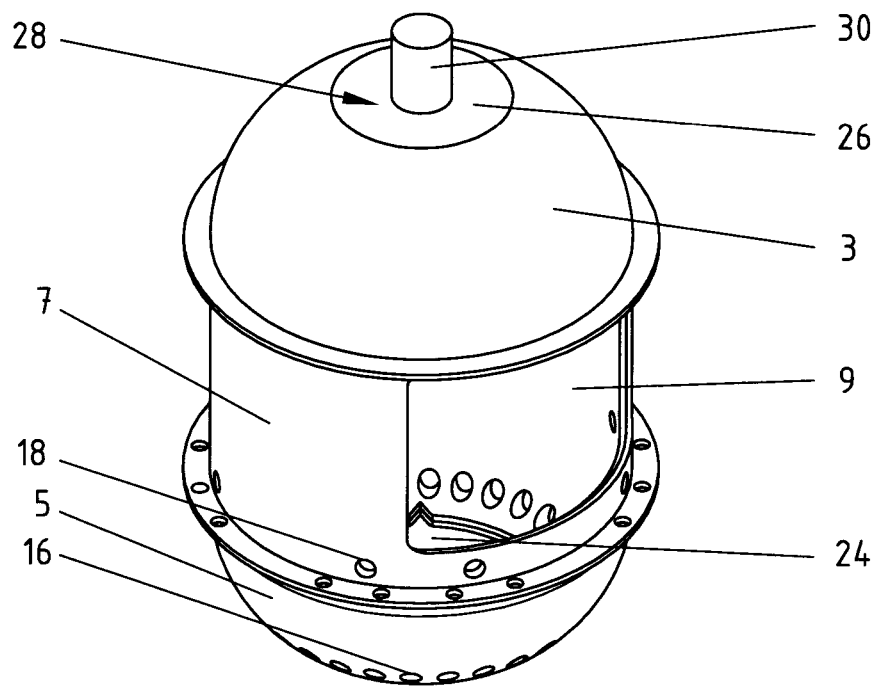
FIG. 10 Perspective view of the illumination device shown in FIGS. 5 to 9 with door omitted.

As it is shown in the illustration of FIG. 10, the detector opening 26 is arranged in an area of the cap 28 of the hemispheric shell 3. For better illustration of the service opening 9 the door 11 is also not shown in the illustration shown in FIG. 10.

Figure 11:
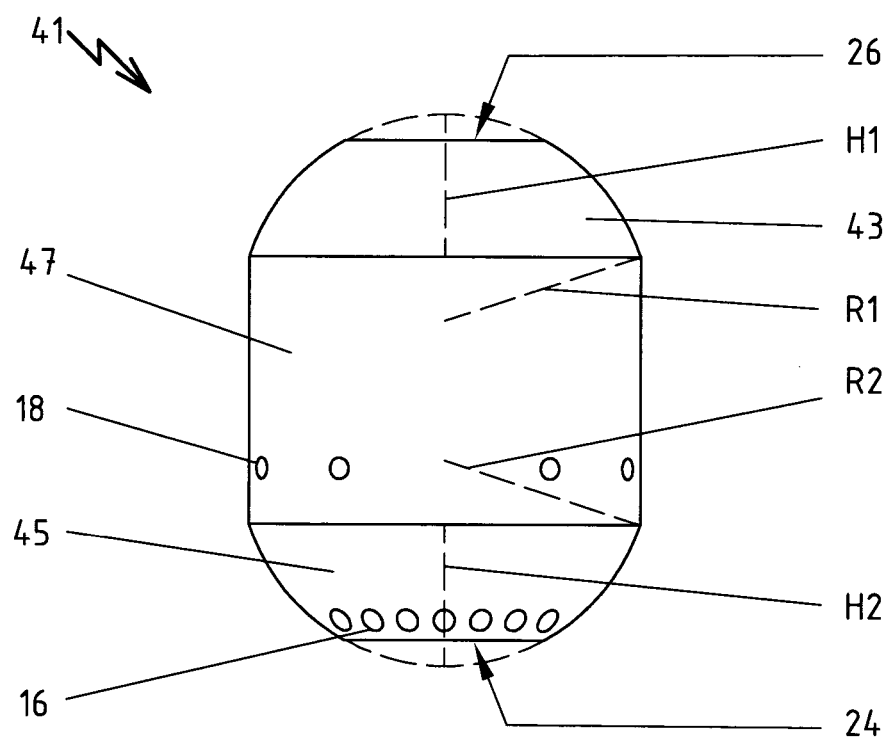
FIG. 11 Schematic illustration of side view of a second embodiment of an illumination device of the present invention.

FIG. 11 shows a further embodiment of an illumination device 41 of the present invention in a front view. In the present case the illustration abstains from showing a service opening. The hollow body in this embodiment is comprised of two spherical caps 43, 45 which again are connected via a hollow cylinder 47. Like the hemispheric shells 3 and 5 shown in FIGS. 5 and 10, which have a uniform radius R, the hemispheric shells 43 and 45 in the example of FIG. 11 are based on spheres having the same radii R1, R2. These radii R1, R2 of the respective spheres in the illustration shown in FIG. 11 are shown using dashed lines. Furthermore, the spherical caps 43 and 45 have identical heights H1 and H2. This provides during the use of spherical caps, which do not represent hemispheric shells, for a comparatively high symmetry and thus a comparatively high isotropy of the light used. In addition, the spherical caps 43, 45 can be connected again in an easy manner via a hollow cylinder 47. This is however also possible when using different radii R1, R2 and different heights H1, H2 for spherical caps 43, 45 if those dimensions are adjusted with respect to each other.

For a better overview, the illustration shown in FIG. 11 does not show illuminants in the drilled holes 16 and 18. But it is possible to use in this case LEDs as they have been used in analogue manner in the embodiment shown in FIGS. 5 and 10.

Like the embodiment shown in FIGS. 5 to 10 also the second embodiment of FIG. 11 comprises an auxiliary opening 24 as well as a detector opening 26.

Figure 12:
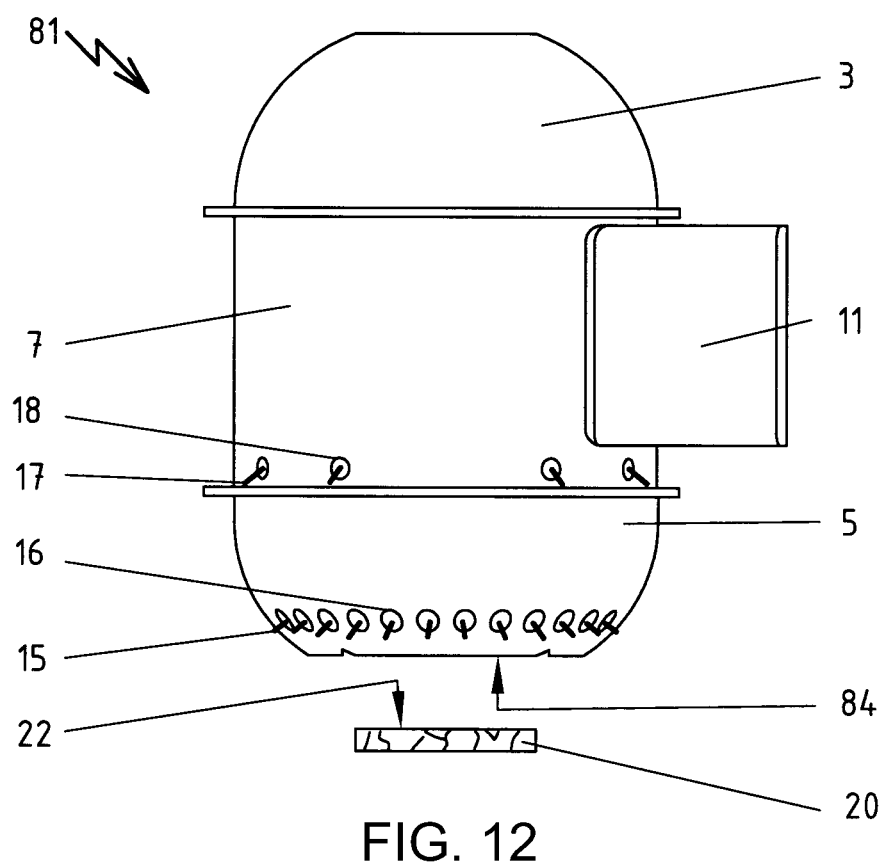
FIG. 12 Side view in a schematic illustration of a third embodiment of an illumination device of the present invention.

FIG. 12 shows a third embodiment of an illumination device 81 of the present invention. This embodiment is largely corresponding to the first embodiment shown in FIGS. 5 to 10. The difference to the first embodiment is that in the third embodiment an auxiliary opening 84 is comprised through which a surface to be illuminated 22 can be illuminated, wherein the surface to be illuminated 22 is positioned outside the hollow body 3, 5, 7. Thus, the auxiliary opening 84 is designed in the present case so that light with a high degree of isotropy, which is the result of multiple reflections at the inner surface, reaches the surface to be illuminated 22 through the auxiliary opening 84. For this reason, the solar cell substrate 20 can be arranged completely outside the illumination device 81 so that it is possible to easily integrate the illumination device 81 into an automated or semi-automated production line. For example, objects with surfaces which are to be illuminated, preferably solar cell substrates, can be transported for examination with a transportation device, such as a conveyor belt, under the auxiliary opening without the need for a complex or at least partial introduction of the objects into the hollow body 3, 5, 7. After the examination is finished, the objects can be further transported along the production line by means of the transportation device. Thus, a discharging process can be omitted.

As described above, for the third embodiment shown in FIG. 12, the degree of isotropy of the light which reaches the surface to be illuminated 22 can be decreased. It has however been shown that the degree of isotropy is in general nevertheless sufficient to circumvent the particle structure. All further developments described in connection with the first embodiment, such as the detector opening 26, can also form part of the third embodiment shown in FIG. 12 so that in this case it can be referred to the corresponding comments with respect to the first embodiment.

Obviously, also the second embodiment shown in FIG. 11 can be equipped in analogue manner to the auxiliary opening 84 as shown in FIG. 12, which illustrates the third embodiment, with an auxiliary opening through which a surface to be illuminated and which is arranged outside the hollow body can be illuminated. Like in the case of the third embodiment, the design of such an auxiliary opening follows the design of the surface to be illuminated.

Finally, it is to be emphasized that those terms, such as spherical cap, tube, hollow cylinder, hemispheric shell and similar references to geometrical figures are to be understood broadly. Therefore, the term spherical cap refers also to such a spherical cap from which the cap area has been removed. Correspondingly, the spherical caps can comprise also in other positions openings or aberrations from the ideal shape of a spherical cap. This applies in analogue manner to the hemispheric shells, the hollow cylinder or the tube. Although deviations from the ideal shape adversely affect the isotropy of the light, the remaining degree of isotropy can in a specific application however be sufficient to adequately circumvent particle structures.

REFERENCE SIGN LIST

1 Illumination device
3 Hemispheric shell
5 Hemispheric shell
7 Hollow cylinder
8 Inner surface
9 Service opening
11 Door
12 Door handle
13 Reflective layer
15 LEDs for indirect illumination
16 Drilled hole
17 LEDs for partially indirect illumination
18 Drilled hole
20 Solar cell substrate
22 Surface to be illuminated
24 Auxiliary opening
26 Detector opening
28 Cap area
30 Camera
41 Illumination device
43 Spherical cap
45 Spherical cap
47 Hollow cylinder
50 Polycrystalline material
51 Particle
52 Particle
53 Particle
54 Conchate disruption
55 Impurity
56 Rupture
60 Integrating sphere
62 Silicum wafer
64 Surface silicum wafer
66 Illuminant
67 Illuminating with isotropic light
68 Detector/Detection
70 Surface texture
72 Antireflection coating
81 Illumination device
84 Auxiliary opening R Radius hemispheric shell
R1 Radius spherical cap
R2 Radius spherical cap
H1 Height spherical cap
H2 Height spherical cap

The invention claimed is:

1. An illumination device for examining an object having a polycrystalline material, the illumination device comprising:
   a hollow body having an inner surface with a light reflecting layer, said hollow body formed of a tube and two spherical caps connected to each other by said tube, thereby providing an inwardly oriented reflecting surface formed from said inner surface and said light reflecting layer following a contour of said tube and said spherical caps; and
   illuminants disposed in said hollow body to illuminate a surface of the object having the polycrystalline material with substantially isotropic light.

2. The illumination device according to claim 1, wherein said spherical caps are based on spheres having a same radius, and said spherical caps being of a same height.

3. The illumination device according to claim 2, wherein said spherical caps are hemispheric shells.

4. The illumination device according to claim 1, wherein said tube substantially corresponds to one of a hollow cylinder and a hollow tube.

5. The illumination device according to claim 1, wherein said hollow body contains a closable service opening.

6. The illumination device according to claim 1, wherein said reflecting layer functions as a Lambertian emitter.

7. The illumination device according to claim 4, wherein said illuminants disposed to illuminate the surface to be illuminated only indirectly.

8. The illumination device according to claim 7, further comprising at least one further illuminant suitable for at least partial direct illumination of the surface to be illuminated.

9. The illumination device according to claim 7, wherein said surface to be illuminated is disposed in one of said spherical caps.

10. The illumination device according to claim 1, wherein one of said spherical caps has an auxiliary opening formed therein through which a surface of the object to be illuminated is capable of being introduced into said hollow body.

11. The illumination device according to claim 1, wherein one of said spherical caps has an auxiliary opening formed therein through which a surface of the object to be illuminated, which is disposed outside said hollow body, is capable of being illuminated.

12. The illumination device according to claim 10, wherein said one spherical cap has a cap and said auxiliary opening is disposed in an area of said cap.

13. The illumination device according to claim 10, wherein one of said spherical caps has illuminants.

14. The illumination device according to claim 1, wherein one of said spherical caps has a detector opening formed therein, said detector opening is disposed in said spherical cap in which neither an auxiliary opening is formed nor a surface to be illuminated is comprised.

15. The illumination device according to claim 14, wherein said one spherical cap has a cap and said detector opening is disposed in an area of said cap.

16. The illumination device according to claim 3, wherein said hemispheric shells have partial spheres with a same radius.

17. The illumination device according to claim 5, wherein said closable service opening is disposed in an area of said tube.

18. The illumination device according to claim 7, wherein said illuminants include different types of illuminants which emit at least partially light of different frequencies.

19. The illumination device according to claim 8, wherein said at least one further illuminant is disposed in said tube.

20. The illumination device according to claim 13, wherein said spherical cap has drilled holes formed therein and said illuminants are disposed in said drilled holes.

21. The illumination device according to claim 20, wherein said drilled holes are formed in said spherical cap having said auxiliary opening.

22. The illumination device according to claim 20, wherein said drilled holes are formed in said spherical cap having the surface to be illuminated.

* * * * *